(12) United States Patent
Levi et al.

(10) Patent No.: US 9,827,447 B1
(45) Date of Patent: Nov. 28, 2017

(54) DEVICES, METHODS, SYSTEMS AND KITS FOR SELECTING SKIN TREATMENT DEVICES

(71) Applicant: Neodyne Biosciences, Inc., Menlo Park, CA (US)

(72) Inventors: Kemal Levi, Mountain View, CA (US); Jasper Jackson, Newark, CA (US); John A. Zepeda, Los Altos, CA (US); William R. Beasley, Los Altos, CA (US); Reinhold H. Dauskardt, Menlo Park, CA (US); Michael T. Longaker, Atherton, CA (US)

(73) Assignee: Neodyne Biosciences, Inc., Newark, CA (US)

( * ) Notice: Subject to any disclaimer, the term of this patent is extended or adjusted under 35 U.S.C. 154(b) by 74 days.

(21) Appl. No.: 13/691,656

(22) Filed: Nov. 30, 2012

Related U.S. Application Data

(60) Provisional application No. 61/566,590, filed on Dec. 2, 2011.

(51) Int. Cl.
*A61B 8/00* (2006.01)
*A61N 7/00* (2006.01)

(52) U.S. Cl.
CPC ..................... *A61N 7/00* (2013.01)

(58) Field of Classification Search
CPC ........................................................ A61N 7/00
USPC .............. 601/1–3; 602/42–54; 606/201–216; 523/111
See application file for complete search history.

(56) References Cited

U.S. PATENT DOCUMENTS

| | | | |
|---|---|---|---|
| 3,613,679 A | | 10/1971 | Bijou |
| 5,549,713 A | * | 8/1996 | Kim .................. A61B 90/02 128/898 |
| 5,662,714 A | * | 9/1997 | Charvin ............... A61F 2/0059 606/187 |
| 7,683,234 B2 | | 3/2010 | Gurtner et al. |
| 2006/0037091 A1 | | 2/2006 | Gurtner et al. |
| 2006/0064024 A1 | * | 3/2006 | Schnall .............. A61B 5/02007 600/500 |
| 2007/0178121 A1 | * | 8/2007 | First ........................ A61K 8/64 424/239.1 |
| 2008/0033334 A1 | * | 2/2008 | Gurtner .................. A61L 15/42 602/50 |
| 2009/0163844 A1 | * | 6/2009 | Gurtner ............ A61K 47/48361 602/53 |
| 2009/0177136 A1 | | 7/2009 | Liedtke et al. |
| 2011/0054283 A1 | | 3/2011 | Shuler |
| 2011/0152738 A1 | | 6/2011 | Zepeda et al. |

(Continued)

OTHER PUBLICATIONS

U.S. Appl. No. 61/443,647, filed Feb. 16, 2011 Jackson et al., titled "Wound or Skin Treatment Devices and Methods".

(Continued)

*Primary Examiner* — Sanjay Cattungal
(74) *Attorney, Agent, or Firm* — Cooley LLP

(57) ABSTRACT

Devices, kits, systems and methods described herein may be for treatment to skin, including but not limited to wound healing, the treatment, amelioration, and/or prevention of scars or keloids. Devices kits, systems and methods described herein may be used to select treatment parameters or devices for treating skin in a zone or region of skin having particular mechanical or other properties.

25 Claims, 9 Drawing Sheets

(56) References Cited

U.S. PATENT DOCUMENTS

| | | | |
|---|---|---|---|
| 2012/0046590 A1* | 2/2012 | Yock | A61B 17/08 602/53 |
| 2012/0226214 A1 | 9/2012 | Gurtner et al. | |
| 2012/0226306 A1* | 9/2012 | Jackson | A61F 13/00 606/201 |
| 2013/0012858 A1 | 1/2013 | Jackson et al. | |
| 2013/0110026 A1 | 5/2013 | Jackson et al. | |
| 2013/0190655 A1* | 7/2013 | Jackson | A61B 5/442 600/587 |

OTHER PUBLICATIONS

U.S. Appl. No. 61/512,340, filed Jul. 27, 2011, Zepeda et al., titled "Skin Straining Device and Method".

Artz et al., "Burns: A Team Approach", (Saunders), Philadelphia, 1979, pp. 24-44.

Barker, D. E., "Skin Thickness in the Human", Plast. Reconstr. Surg., vol. 7, 1951, pp. 115-116.

Gurtner et al., "Improving Cutaneous Scar by Controlling the Mechanical Environment: Large Animal and Phase I Studies", Annals of Surgery, vol. 00, No. 00, 2011, pp. 1-9.

Lee, Y., "Skin Thickness of Korean Adults", Surg. Radiol. Anat., vol. 24, 2002, pp. 183-189.

Marcellier et al., "Optical Analysis of Displacement and Strain Fields on Human Skin", Skin Res. Technol., vol. 7, 2001, pp. 246-253.

Staloff et al., "Measurement of Skin Stretch Using Digital Image Speckle Correlation", Skin Res. Technol., vol. 14, 2008, pp. 298-303.

Final Office Action received for U.S. Appl. No. 13/791,728, dated Nov. 4, 2015, 9 pages.

Non-Final Office Action received for U.S. Appl. No. 13/791,728, dated Apr. 22, 2015, 10 pages.

Advisory Action received for U.S. Appl. No. 13/791,728, dated Jan. 22, 2016, 3 pages.

Non-Final Office Action received for U.S. Appl. No. 13/791,728, dated May 26, 2016, 9 pages.

* cited by examiner

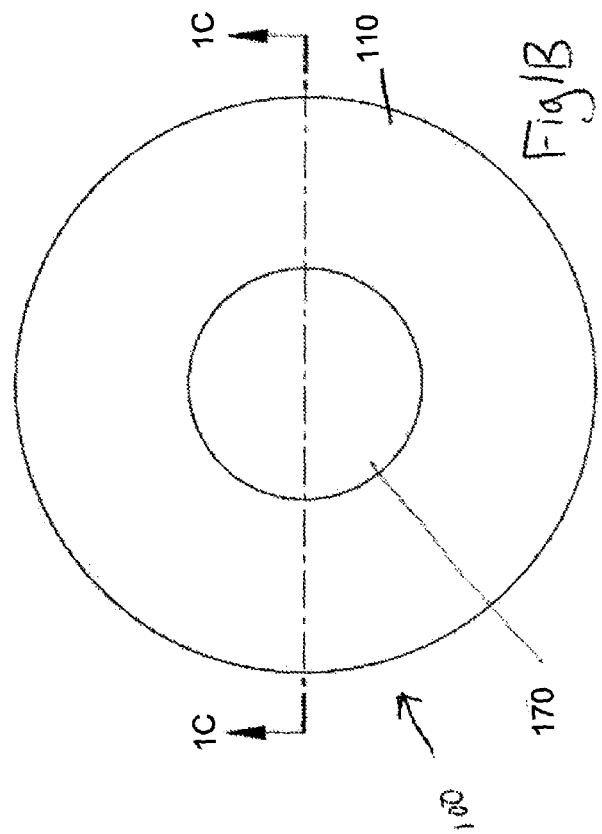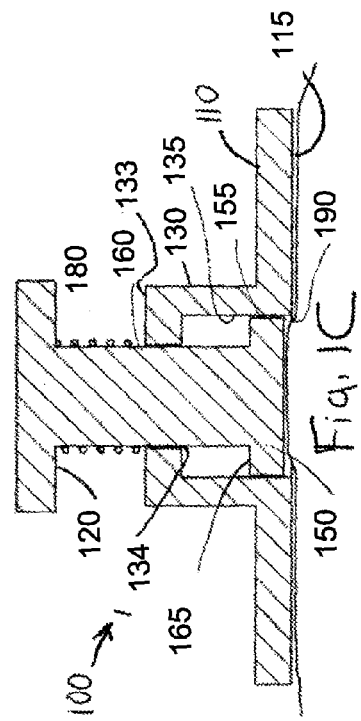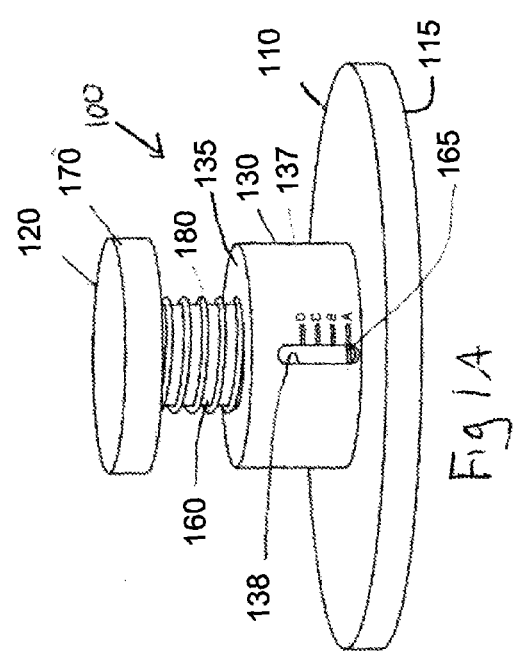

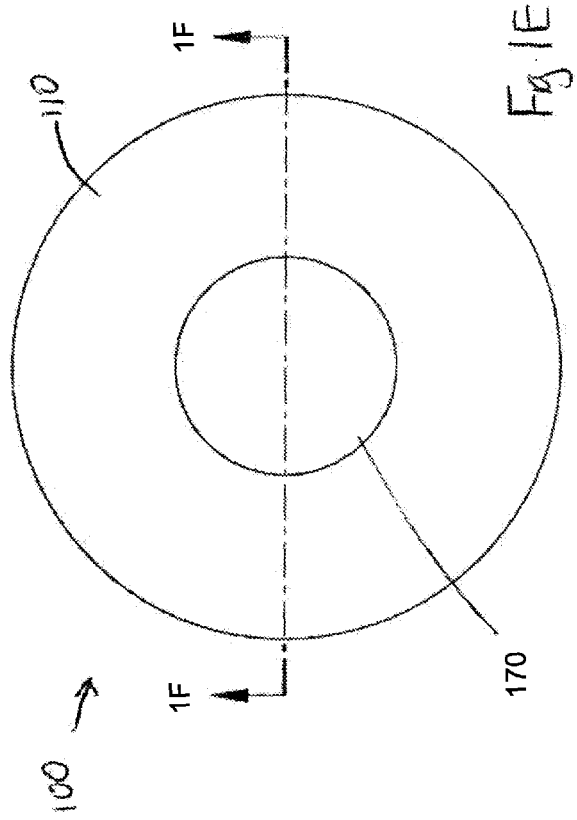
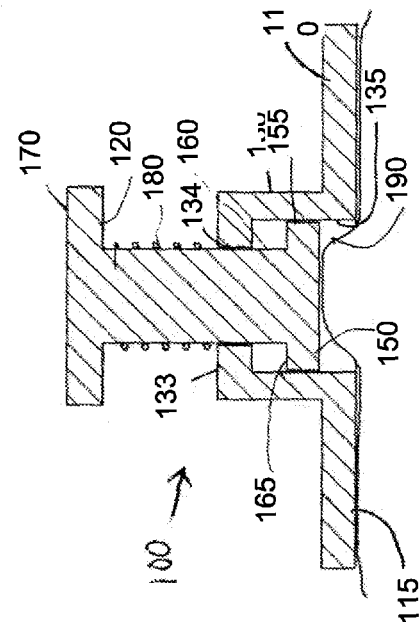
Fig 1E
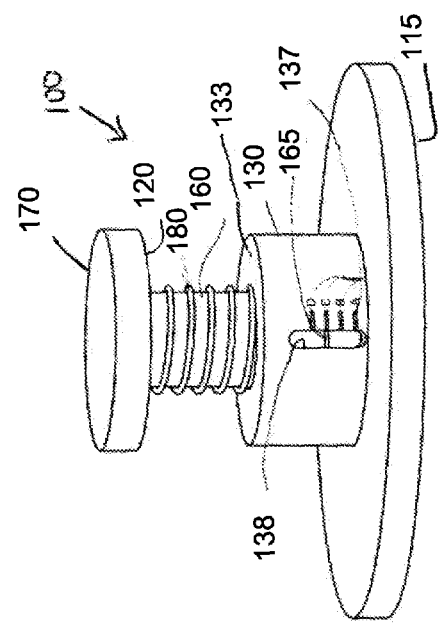
Fig 1F
Fig 1D

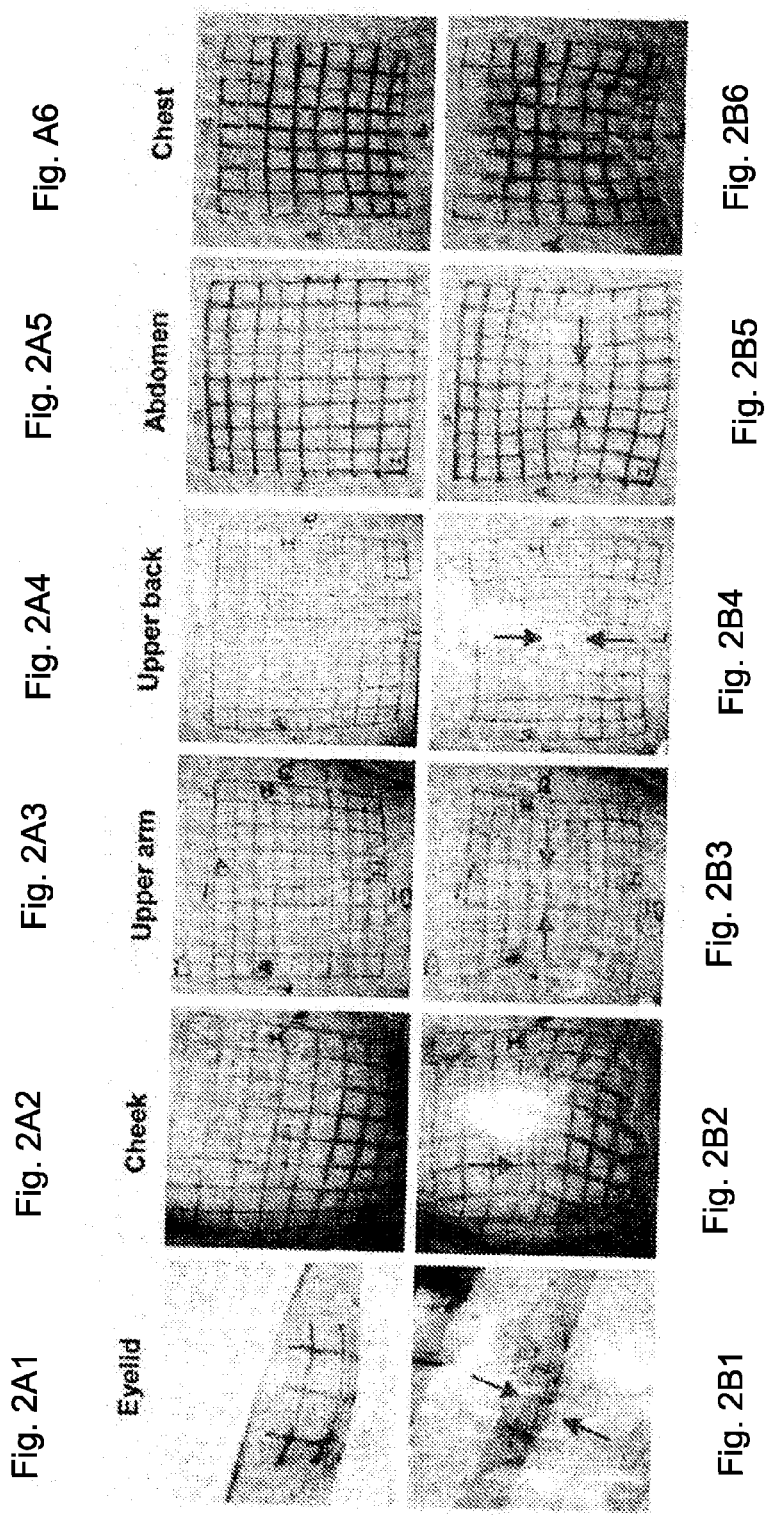

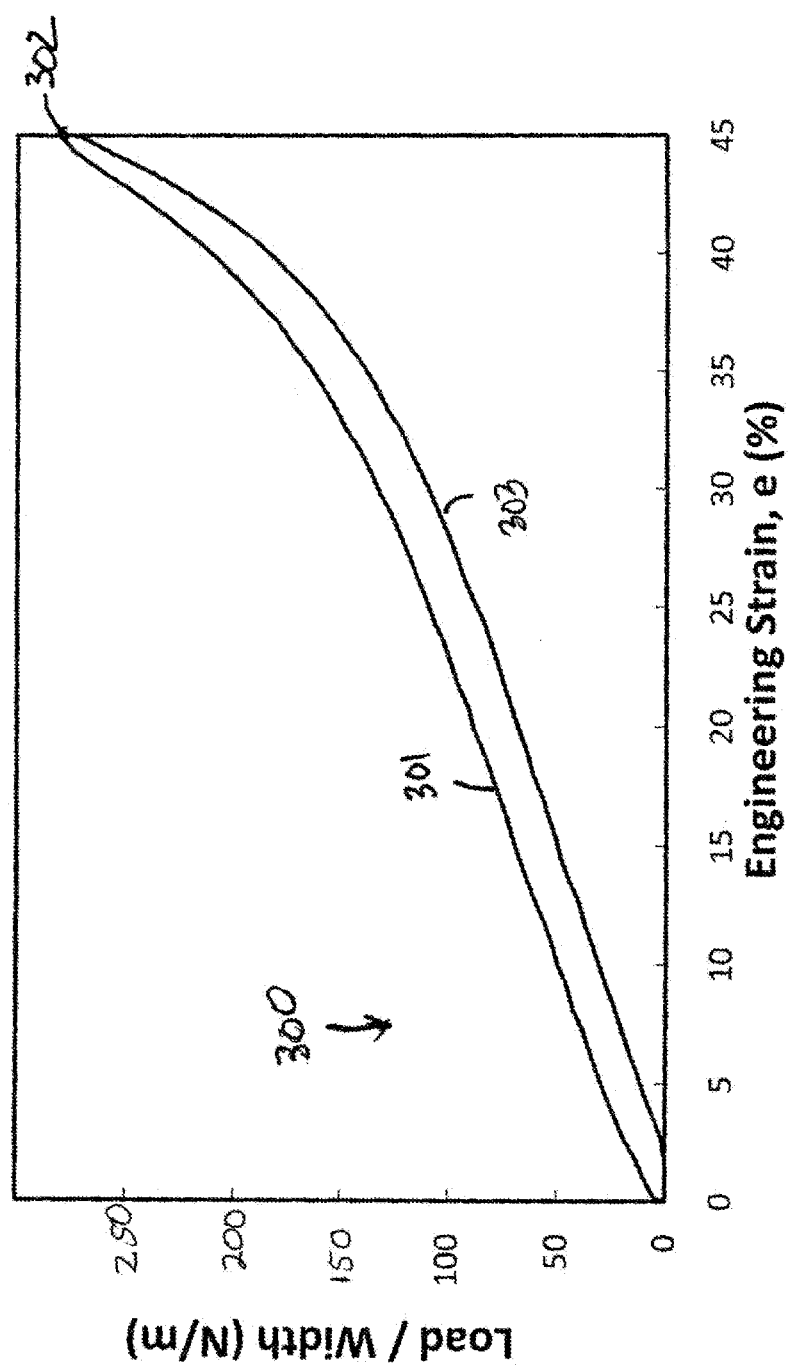

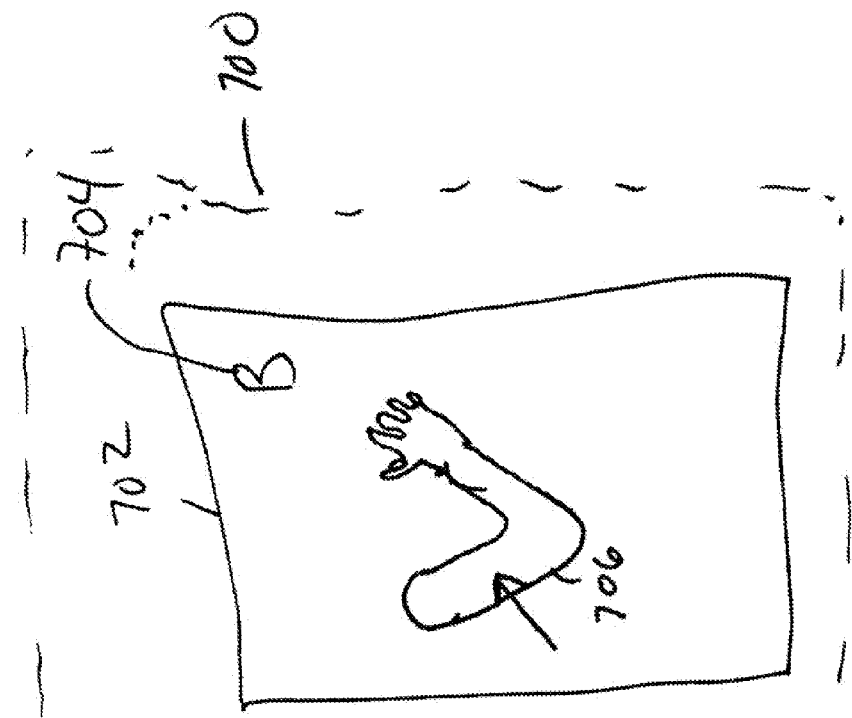
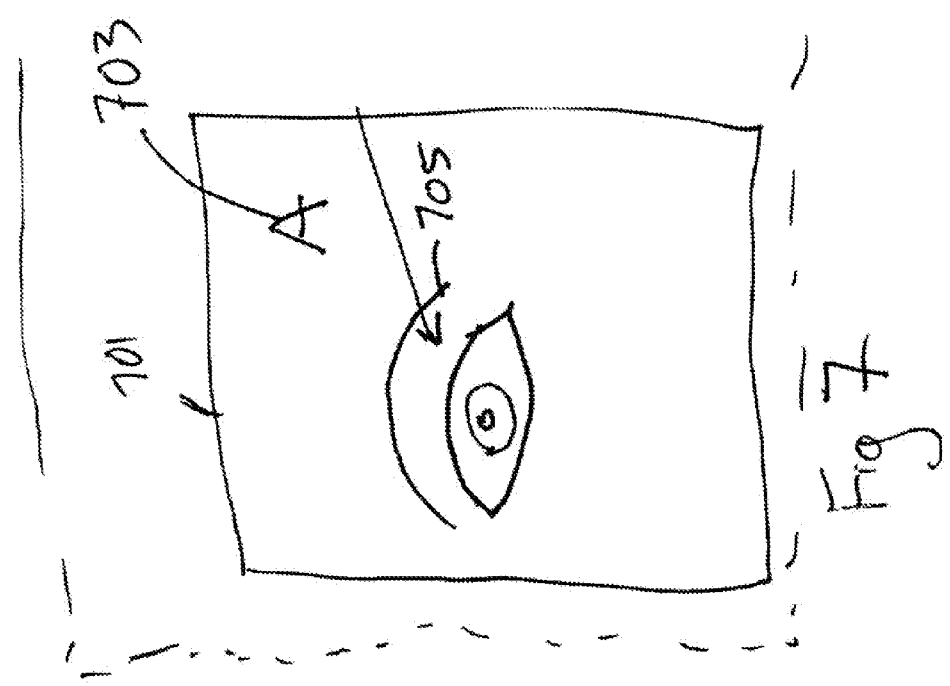
Fig 7

DEVICES, METHODS, SYSTEMS AND KITS FOR SELECTING SKIN TREATMENT DEVICES

CROSS-REFERENCE TO RELATED APPLICATIONS

This application claims the benefit of 35 U.S.C. §119(e) to U.S. Provisional Application Ser. No. 61/566,590 filed on Dec. 2, 2011, which is hereby incorporated by reference in its entirety. This application is also related to U.S. application Ser. No. 11/888,978, now U.S. Pat. No. 7,683,234, filed on Aug. 3, 2007; U.S. application Ser. No. 12/358,159, now U.S. Pat. No. 8,063,263, filed on Jan. 22, 2009; U.S. application Ser. No. 12/358,162, now U.S. Pat. No. 8,168,850, filed Jan. 22, 2009; U.S. application Ser. No. 12/358,164, now U.S. Pat. No. 8,183,428, filed Jan. 22, 2009; U.S. application Ser. No. 13/089,104, filed Apr. 18, 2011; U.S. application Ser. No. 13/089,105, filed Apr. 18, 2011; U.S. application Ser. No. 12/854,859, filed Aug. 11, 2010; U.S. application Ser. No. 13/089,129, filed Apr. 18, 2011; U.S. application Ser. No. 13/315,214, filed Dec. 8, 2011; and U.S. application Ser. No. 13/029,023, filed Feb. 16, 2011.

FIELD

The claimed invention relates to devices, methods, systems and/or kits for selecting skin treatment devices or device properties based on skin properties.

BACKGROUND

Scar formation in response to cutaneous injury is part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and may occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress may increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

BRIEF SUMMARY

Devices, kits and methods described herein may be for skin treatment where it is desirable to manipulate, or alter inherent or endogenous stresses within skin and/or to control or manipulate an effect of exogenous stresses on skin. Such treatment may include, but is not limited to wound treatment or the treatment, amelioration, or prevention of scars and/or keloids and/or treat wound dehiscence. According to the devices, kits and methods described herein, a device may be attached to or coupled to one or more layers of the skin or tissue of a subject.

According to variations, a method may be provided for treating a subject comprising: identifying a location on a body of a subject for deployment of a skin treatment device; selecting a skin treatment device from a plurality of skin treatment devices wherein each of the plurality of skin treatment devices has a different mechanical property and is associated for use with a body region; and attaching the skin treatment device in the initial strained configuration to the treatment site. According to a variation, each of the plurality of skin treatment devices associated for use with a body region may be packaged with a label indicating the body region. According to a variation, the label may graphically indicate the body region.

According to variations, a method may be provided for selecting a skin treatment device for a subject based on one or more inherent skin properties, comprising: providing a skin interface element configured to apply an energy to skin of a subject; applying an energy to the skin of a subject; determining a skin mechanical property of a skin location of a subject; providing a plurality of skin treatment devices each of the plurality of devices comprising an elastic member and a securing member configured to couple the device to skin of a subject, wherein each of the plurality of skin treatment devices has a relaxed configuration and an initial strained configuration; wherein each of the plurality of skin devices has a different device mechanical property; and selecting one of the plurality of skin devices based at least in part on the determined skin mechanical property of the skin location; and attaching the skin device in the initial strained configuration to the skin of the subject. The step of applying energy comprise applying a mechanical force; a vibrational energy; and/or acoustic energy or other energy.

According to variations, a method of treating a subject is provided comprising: determining a skin mechanical property of a skin location of a subject; selecting an initial strain amount to be applied to a skin treatment device based on the location, wherein the skin treatment device comprises an elastic member configured to be stretched; and applying the initial strain amount to the skin treatment device; then applying the skin treatment device to the skin of a subject. According to variations, the skin mechanical property may comprise an inherent skin tension, a relative skin tension, skin stiffness, and/or a skin deformation property.

According to variations, a method is provided for treating a subject comprising:

identifying a location on a body of a subject for deployment of a skin treatment device of a treatment site; selecting an initial strain amount to be applied to a skin treatment device based on the location, wherein the skin treatment device comprises an elastic member configured to be stretched; and applying the initial strain amount to the skin treatment device; then applying the skin treatment device to the skin of a subject. According to variations, the method may further comprise identifying one or more mechanical properties of a skin location for treatment.

According to variations, a system is provided for treating a subject comprising: a plurality of skin treatment devices wherein each of the plurality of skin treatment devices has a different mechanical property from the other of the plurality of skin treatment devices; and a skin property determining device configured to determine a skin mechanical property, wherein the skin property determining device comprises a plurality of indicators configured to indicate one of the plurality of skin treatment devices. According to variations, the skin property determining device may comprise a skin tension device configured to determine a relative inherent skin tension.

According to variations a system is provided for treating a subject comprising: a skin treatment device comprising an elastic member wherein the elastic member has a relaxed configuration and a plurality of selectable strained configurations; and a skin tension device configured to determine a relative skin tension, wherein the skin tension device comprises a plurality of indicators configured to indicate one of the plurality selectable strained configurations.

According to variations, a system is provided for treating a subject comprising: a skin treatment device comprising an elastic member wherein the elastic member has a relaxed configuration and a plurality of selectable strained configurations; and a tensioning member configured to strain the skin treatment device to the plurality of selectable strained configurations, and an strain selector configured to indicate a selected one of the plurality of selectable strained configurations. The strain selector may be configured to indicate a strain for a particular region of the body.

According to variations a method may be provided for treating a subject with a skin treatment device comprising: stretching an elastic member from a relaxed configuration to an initial strained configuration, wherein the initial strained configuration is a predetermined amount of strain selected for a particular region of application to provide an approximate desired resulting load per width the skin location; and securing the elastic member to a skin location of a subject at the particular region to provide the approximate desired resulting load per width at the skin location. The approximate desired resulting load per width may be, for example, between about 2 and 5 N/m, between, between about 28 and 48 and/or between about 47 and 80 N/m.

BRIEF DESCRIPTION OF THE DRAWINGS

FIG. 1A is a perspective view of a skin strain measuring device in a first configuration in accordance with a variation of the invention.

FIG. 1B is a top view of the skin strain measuring device of FIG. 1A in the first configuration.

FIG. 1C is a side cross-sectional view of the skin strain measuring device of FIGS. 1A and 1B along the lines A-A.

FIG. 1D is a perspective view of a skin strain measuring device of FIG. 1A in a second skin tensioning configuration.

FIG. 1E is a top view of the skin strain measuring device of FIG. 1D in the second skin tensioning configuration.

FIG. 1F is a side cross-sectional view of the skin strain measuring device of FIGS. 1D and 1E along the lines B-B.

FIGS. 2A1 to 2A6 are photographs of grid lines applied to various regions of skin.

FIGS. 2B1 to 2B6 are photographs of the grid lines of the various regions of skin of FIGS. 2A1 to 2A6 after application of skin treatment device to a subject.

FIG. 3 is a schematic curve generally representing the force versus strain of a skin treatment device during loading and unloading of a skin treatment device.

FIG. 6 is a graphical representation of estimated stress vs. strain values.

FIG. 7 is a schematic illustration of a plurality of labeled and packaged skin treatment devices.

DETAILED DESCRIPTION

Figure 4:
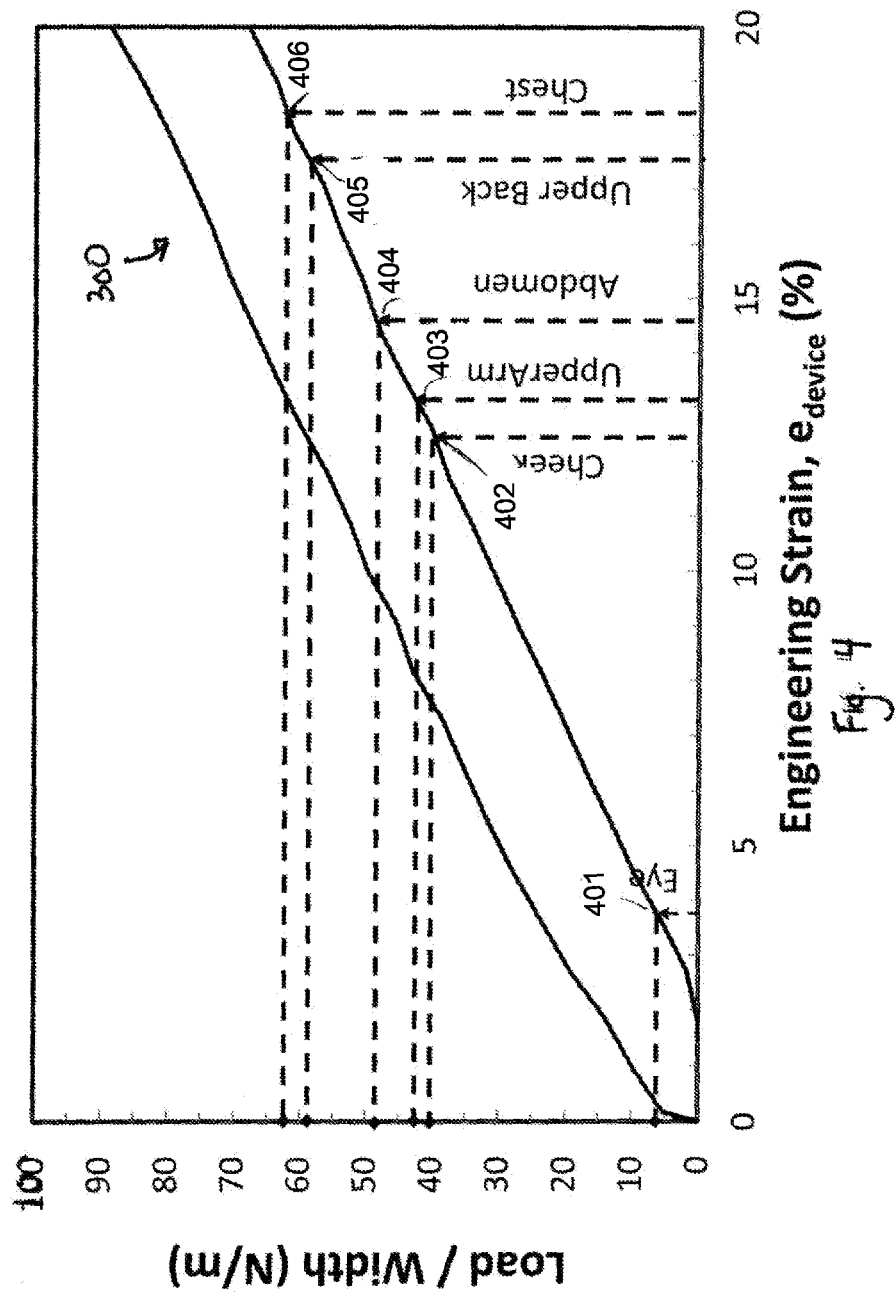
FIG. 4 is an enlarged section of the curve of FIG. 3.

According to the devices, kits and methods described herein, a skin treatment device, skin device, wound treatment device, scar or keloid treatment device, scar or keloid amelioration or prevention device, bandage, or dressing may be provided that may be applied, attached to or coupled to one or more layers of the skin or tissue of a subject (hereinafter referred to as "dressing", "skin device" or "skin treatment device").

It is believed that controlling, managing or modulating stresses acting in and/or on skin ("mechanomodulation") may have beneficial effects. Modulation of mechanical stresses or effects acting in and/or on skin may translate into or induce biomechanical response, including but not limited to, responses relating to scarring, scar proliferation or other effects.

Devices, methods, systems and kits described herein may relate to devices used to shield skin or a wound from its mechanical environment. The term "shield" is meant to encompass the unloading of stress experienced by the skin or wound as well as and/or providing a physical barrier against contact, contaminants, and the like. The stress shielding or force offloading devices and methods described here may shield the skin or a wound by unloading endogenous stress and/or exogenous stresses. In some variations, the devices may shield the skin from endogenous stress without affecting exogenous stress on the skin, e.g., devices that modify the elastic properties of the skin, etc. In other variations, the devices may shield the wound from exogenous stress without affecting endogenous stress on the skin wound. In still other variations, the devices shield the skin from both endogenous and exogenous stress.

Devices, kits and methods described herein may treat skin at a skin site ("skin treatment device"), including without limitation, to ameliorate the formation of scars at wound sites by controllably stressing or straining the epidermis and deeper layers of dermal tissue at or near a skin site, i.e., at or adjacent a wound or treatment site of a subject's skin, thereby reducing tensile or compressive stress at the skin site. The stress at the skin site may be reduced to levels below that experienced by normal skin and tissue. The stress or strain may be applied to surrounding tissue in one, two, or more directions to reduce endogenous or exogenous stress at the skin site in one, two or more directions. Thus, devices and methods described herein may reduce the stress experienced by skin and/or a wound and surrounding tissues in order to treat a subject. The device may also assist in preventing or reducing the incidence of wound dehiscence.

Devices, kits and methods described herein may be for the treatment, amelioration, or prevention of scars and/or keloids by creating and/or maintaining a pre-determined strain in an elastic skin treatment device that is then affixed to the skin surface using skin adhesives to transfer a generally planar (e.g. compressive) force from the bandage to the skin surface. Other uses include wound closure and skin splinting/stabilization treatments.

In some variations, a dressing is provided, comprising an elastic sheet structure (e.g., a comprising a silicone polyurethane, TPE (thermoplastic elastomers), synthetic rubber or co-polyester material) comprising an upper surface, a lower surface, a first edge and a second edge opposite the first edge, and one or more adhesive regions. The dressing may further comprise a first release liner releasably attached to the adhesive region or regions. The adhesive region(s) may comprise a pressure sensitive adhesive. The dressing may be tapered or otherwise shaped to reduce skin tension at the edges. The dressing may have modified, reduced or no adhesive near its edges to reduce skin tension at the edges. Portions of the dressing may be unstrained and may thereby reduce strain in certain areas of the skin where the dressing is applied. In some specific examples, the unstrained area or areas are found between the edges of the dressing and the strained area(s). In some further examples, the unstrained areas are limited to this area and are not found, during application or use, between the strained areas of a single dressing, in use. In still further examples, the unstrained areas are limited to areas along the edges of a dressing that intersect the strain axis of the strained area(s), but not to areas along the edges of the dressing that are generally parallel to the strain axis.

A device may be used to strain and/or maintain a strain on a dressing. The device may further comprise a releasable locking mechanism, attachment mechanism or adhesive, configured to maintain the member or mechanism in a strained configuration. An applicator or tensioning device may be used strain, tension, and or apply a device to a subject.

In addition to amelioration of scar formation, other uses for such skin treatment device may or may not include without limitation, for example, treating skin related conditions such as acne, blemishes, rosacea, warts, rashes (including but not limited to erythematous, macular, papular and/or bullous conditions), psoriasis, skin irritation sensitivity, allodynia, telangiectasia, port wine stains and other arteriovenous malformations, and ectopic dermatitis; treating or improving existing scars, wrinkles, stretch marks, loose or sagging skin or other skin irregularities; lifting pinning, holding, moving skin for various purposes such as during pre-operative preparation, during surgical procedures for example as a low profile tissue retractor, to stabilize blood vessels during needle or catheter insertion, postoperatively, pre or post operatively for pre-treating or preconditioning skin for example, prior to scar revision, wound incision, body contouring, in mastectomy skin expansion, aesthetic skin treatment or resurfacing whether topical or subdermal, whether or not using an energy modality such as, for example, microwave, radio-frequency ablation, high-intensity focused ultrasound, laser, Infrared, incoherent light, thermal (heat and/or cold, ablative or nonablative), use of vacuum or suction, vibration or massage (e.g. ENDERMOLOGIE®, LPG Systems, France), during weight loss, or for aesthetic purposes; hair removal or hair loss; treating and/or closing skin injuries for example, incisions, wounds, chronic wounds, bed sores, ulcers (including venous stasis ulcers), preventing or reducing the incidence of wound dehiscence, diabetic skin or wound conditions, burn healing and/or relief; acting as an occlusive or negative-pressure wound dressing; protecting incisions or wounds, e.g. prevention of splitting or opening, protecting newborn belly buttons after cutting umbilical cord. Such treatments may include use of a drug or other therapeutic agent that may be applied to the skin with such device. The agents may include but are not limited to antibiotics, anti-fungals, immune modulators including corticosteroids and non-steroidal immune modulators. The agents may be provided in any of a variety of formulations, including but not limited powders, gels, lotions, creams, pastes, suspensions, etc. The devices may also be used for purposes of delivering a drug to the skin or through the skin, for example by stretching the skin and applying a drug thereto. Different configurations of the device may be amenable to the size or geometry of different body regions. The treatments may be applied to regions of any shape (e.g. linear, curved, stellate), size or depth, and to one or more regions of the body, including but not limited to the scalp, forehead, face (e.g. nose, eyelid, cheeks, lips, chin), ears, neck, shoulder, upper arm, lower arm, palm, dorsum of the hand, fingers, nailbed, axilla, chest, nipple, areola, back, abdomen, inguinal region, buttocks, perineal region, labia, penis, scrotum, thigh, lower leg, plantar surface of the foot, dorsal surface of the foot, and/or toes. Such devices may also be referred to herein as a "dressing", "skin device" or "skin treatment device".

"Dressing" or "Skin Device" as used herein may include but is not limited to a skin treatment device, wound treatment device, scar or keloid treatment device, scar or keloid amelioration or prevention device, bandage, or dressing, that may be applied, attached to or coupled to one or more layers of the skin or tissue of a subject.

Various material and mechanical properties of skin, including but not limited to, e.g., skin thickness, elasticity, compression modulus, tension modulus, stiffness, inherent stress and/or strain, may vary across different body regions (including but not limited to for example, face, eyelid, cheek, forehead, chin, lips, shoulder area, upper arm, lower arm, hands, fingers, ear, upper back, lower back, buttocks, upper abdomen, lower abdomen, thigh, upper leg, lower leg, chest, knee, thigh, calves, head, neck, breasts) and/or from subject to subject based on individual skin characteristics or among other things, depending on various demographic factors including but not limited to age, sex, race, body mass index, changes in weight, sun exposure, dietary habits, environmental factors, smoking and other health related issues. A region with less inherent tension may require less force to strain skin or unload forces or tension a given amount. For example, a location such as an eyelid may have less inherent stress or tension in the skin than for example, an abdomen of the same subject. Thus, such a skin site or zone may require less force to strain skin (in tension or compression) or unload forces or tension a desired amount, than the zone with higher inherent stress or tension. On the other hand, a region with greater inherent tension may require greater force to strain skin or unload forces or tension a desired amount. A skin location on one subject may have greater or lesser tension than on another subject at a similar location.

According to variations, a device may be used to determine a relative skin tension at a particular skin region or location of a subject. Based on this relative determination, a device or devices may be selected to impart a desired, approximated or estimated amount of strain or off-loading of stresses at a skin site. According to variations, a relative tension measurement may be made pre-operatively, on healthy skin, on skin adjacent a wound to be closed, immediately post-closure, and/or at any step during the healing process. According to variations, a tension measuring device may be used to check skin tension after skin device application, for example, to confirm adequacy of selection and/or placement of the skin device. According to variations, periodic monitoring may be performed over a period of use of a skin device and/or over a period of healing and scar formation. According to variations, the device or procedure may be used to assess how or how tight to tension sutures.

According to variations, one or more mechanical force properties of a skin shielding device may be selected for use based on an estimated or measured relative inherent skin tension (or other mechanical skin properties) of a particular skin site, skin area or skin zone.

One or more such device mechanical properties may include but is not limited to strain value of the device, imparted skin strain by the device depending on skin site, load or force per width, stress strain relationships in loading or unloading and/or device stiffness, modulus of elasticity, loss modulus, storage modulus, complex modulus, durometer, hardness, creep and stress relaxation characteristics.

Such device or device properties may be, among other things, based on measurements of skin properties, estimated based on location of a skin site to be treated, estimated based on patient demographic information, and/or estimated based on measurements at one or more particular skin zones, e.g., locations on a particular subject's body.

Such device or device properties may be selected based on a desired amount of stress offloading, a desired skin strain and/or desired forces on the skin outside the skin treatment device, adjacent the skin treatment device, and/or at the edges of the skin treatment device. It is believed that in some subjects, skin irritation may be reduced where the stress at the edge of the device is lower. According to variations one or more mechanical properties of a skin treatment device may be selected to be within a range where the device unloads a sufficient amount of tension to treat the skin or wound while having sufficiently low edge stresses to reduce skin irritation.

According to variations, skin may be selectively mechanomodulated using one or more devices or methods. A skin treatment device may be a pre-strained (e.g., at point of manufacture or for a period of time prior to use) to a particular force or strain level. The pre-strained device with the desired force level or strain may be selected for a particular skin zone and/or a particular subject.

A skin treatment device may be strained by a user with a tensioning (stretching) device, or an applicator. Such tensioning device may provide a predictable amount of strain and/or a particular force to a skin treatment device. Thus, a tensioning device may be selected from one or more tensioning devices with different force or strain application properties. A tensioning device or applicator may also provide a various selectable amounts of force or strain to a skin device. Such tensioning device may be configured to allow a user to select an amount of stress, strain or force to be applied to a skin treatment device which may be selected for a particular skin zone and/or a particular subject. In some variations a skin treatment device may be applied to pre stressed or pre-strained skin where the level of stress or strain in the skin may be pre-selected based on similar factors. Examples of tensioning devices, applicators, pre-strained devices and skin pre-straining devices and methods are set forth in U.S. application Ser. Nos. 12/854,859, 13/029,023; 61/443,647; and 61/512,340 which applications are incorporated in their entirety herein by reference.

According to variations, device materials and/or construction of a plurality of skin treatment devices may individually vary where at a given preset percent strain, each skin treatment device may exhibit a different force property. One of the plurality of skin treatment devices at such predetermined strain may be selected based on a given force profile for the skin device (at a particular initial strain level).

Referring to FIGS. 1A to 1F, a skin tension measuring device 100 is illustrated comprising a skin platform 110 coupled to a cylindrical portion 130, and a spring-loaded plunger 120 movably or slideably positioned through the cylindrical portion 130. The skin platform 110 and cylindrical portion define a chamber 140 for receiving the plunger 120. The plunger 120 comprises plunger handle 170 coupled to a post 160 and plunger end 150. The plunger handle 170 is positioned outside of the cylindrical portion 130; the post 160 slides through an opening 134 through the top 133 of the cylinder 130; and the end 150 is positioned within a cavity 135. An outwardly biased spring member 180 having a known spring constant is positioned between the plunger handle 170 and the top 133 of the cylindrical portion 130 where it engages the plunger handle 170 and the top 135 of the cylindrical portion 130. The spring member 180 tends to move the plunger 120 upwardly.

The plunger 120 is shown in an initial loaded position in FIGS. 1A to 1C. The bottom side 115 of the skin platform 110 is positioned on skin at a skin location or zone to be tested. The plunger 120 is depressed so that the end 150 of the plunger 120 is against an area of skin 190 to be tensioned by the plunger 120. The side 155 of plunger end 150 substantially sealing engages the inner wall 135 of the chamber 140 so that when the plunger 120 is released, a vacuum type force is created between the skin area 190 and the end 150 of the plunger 120. In the configuration shown in FIGS. 1A to 1C with the plunger depressed by a user, the skin area 190 is un-tensioned while the spring member 180 is tensioned.

As shown in FIGS. 1D to 1F, the plunger 120 is released whereby the spring member 180 biases the plunger handle 170 upward. Tension in the skin area 190 counteracts the spring tension to reach equilibrium. Thus, the amount that the spring member 180 moves the plunger 120 upward corresponds or may be correlated to the inherent tension in the skin at the area 190. Accordingly the deflection or the change in distance of the plunger 120 may correlate to the inherent tension in the skin The cylinder 130 includes a window 138 through which the vertical position of the top 165 of the end 150 of the plunger 120 may be visible. Vertically spaced indication lines 137A to 137D are located on the cylinder 130. The vertically spaced indication lines 137A to 137D correspond or correlate to relative skin tension amounts or levels. According to a variation, the top 165 of the end 150 is aligned with the indication line 137A when the plunger 120 is depressed and the end 150 is positioned on the area of skin 190. When the skin is tensioned for example, as shown in FIGS. 1D to 1F, the indication lines 137 A to D may be used to identify or elect a type or force properties of elastomeric device to be applied to the skin (or desired skin pre-straining level), i.e., based on the inherent tension in the skin at the skin site or area of skin 190. The elastomeric device type may be a device having a predetermined amount of force at a pre-determined level of strain. It may be a device with a predetermined amount of strain. The lines may also indicate to a user an amount of strain to apply to a particular skin treatment device before applying it to the surface of a skin. The lines may also indicate an amount of strain to pre-apply to skin before applying a skin treatment device that is un-tensioned or tensioned by particular amount. For example, a skin treatment device as described in U.S. Pat. No. 7,683,234 (incorporated in its entirety without limitation herein by reference), may be used. Also as described in Co-pending application Ser. No. 12/854,859 entitled "Devices and Methods For Dressing Applicators", application Ser. No. 13/345,524 entitled "Wound or Skin Treatment Devices and Methods", application Ser. No. 13/411,394, or application Ser. No. 13/411,443, (incorporated in their entirety without limitation herein by reference), an applicator may be used that may permit selecting the amount of strain applied to a skin treatment device. Additionally, an amount of pre-strain to be applied to skin may be selected as shown in co-pending application Ser. No. 13/029,023 entitled "Skin Straining Devices and Methods" (incorporated in its entirety without limitation herein by reference).

In use, the skin platform 110 is attached in the first to a skin area 190 for testing with a high tack adhesive such as a PSA. In the initial configuration, the plunger 120 is depressed and the spring loaded and locked into an initial position. Once the skin platform 110 is secured, the spring member 180 is released and the skin is tensioned as illustrated in FIGS. 1D to 1F. The user reads the location of the top of the plunger end 150 and determines based on the location with respect to one or more indication lines 137A to 137D, how to treat a subject, i.e. which skin treatment device, strain level, or force level to apply to pre-strain a skin treatment device or to pre-strain skin. The device 100 may then be removed or peeled off the skin.

The line A is shown when the plunger 120 is fully depressed. The line B may indicate a greater mechanical skin property or inherent skin tension and the use of a skin device configured to provide or deliver relatively greater force to the skin at the surface. Line C may indicate a mid-range mechanical skin property or inherent skin tension and the use of a skin device configured to provide or deliver a relatively mid-range force to the skin at the surface. Similarly, line D may indicate of a lower inherent skin tension and the use of a skin device configured to provide or deliver relatively less force to the skin at the surface.

FIG. 7 illustrates a plurality of packages 701, 702 of a plurality of skin treatment devices associated for use with a body region with a label 703, 704 respectively indicating the body region. Alternatively or additionally, graphic indicators of body locations 705, 706 respectively may be provided. The device 701, 702 may or may not be packaged together in a package 700. The may be packaged individually or in other groupings. Devices may be labeled with other indicia with or without body region indicia. For example devices may be labeled with colors, letter, numbers or other indicia that correlate the device to a particular use, mechanical property, and/or patient demographic or any combination of, location, relative range or amount of the foregoing.

The information may also be used to determine and/or to compare a relative skin tension at one skin site versus another location or an average skin site or a standard. For example, the tension at the abdomen may guide the user to select a device for a subject's back or eyelid (knowing relative similarities or differences in skin regions of a subject for example as described herein). Tension at one site may be used to determine or approximate tension at a location where such measurement may be more difficult, or where a wound is present and where it would be undesirable or not feasible to measure inherent tension of skin. A measurement may also be taken at a region that is expected to be similar to the location where the device is to be used. Also, a measurement may be taken at a region with an expected difference or delta with respect to the location where the device is to be used, ant the measurement may be used to estimate or select or help identify a device or device property to be selected. For example, the device may be used to determine if the skin location exhibits a greater, lesser or typical tension as compared with an average or standard e.g., for a particular region or demographic.

In the following example, it is shown that location or zone specific variation in skin biomechanical properties may be characterized using non-invasive technologies. With respect to formation of scars that may be affected by the biomechanical properties of a skin location or zone, there may be some locations that have higher inherent stress levels and may thus have higher wound stress levels and may accordingly be more pre-disposed to scar formation or scar proliferation than others. Accordingly, there may be specific force properties or ranges of force properties of skin treatment devices that may be selected based on a particular skin location or zone.

Example I

To characterize regional differences in human skin mechanical properties, inked grids were placed at various locations, zones or sites on the skin of three healthy human male subjects. Then, skin treatment devices described below were applied to the skin sites and compressive skin strain levels were determined as described below.

The skin treatment or stress shielding devices were silicone devices constructed of SSF-MLTN-950 by Specialty Silicone Fabricators, Inc. (Paso Robles, Calif.). The samples were initially about 2"×1" with a thickness of 0.010"±0.001. A pressure sensitive skin adhesive, made of MD 4502 PSA (Manufactured by Dow Chemical, Inc.) of about 0.004" to about 0.006" thick was applied to a skin interfacing surface of the devices. The samples had a durometer value of about 45 to 55 (Shore A scale), a tensile strength of about 1,535 psi, elongation of about 719% and a specific gravity of about 1.11 to 1.16. (In other examples, the device material may have a durometer value of about Shore A 15 to about 90, sometimes about Shore A 35 to 75 and other times about Shore A 50 to 60, or Shore a 50 to 75.)

The skin treatment device was used to impose compressive strains on unwounded skin of three healthy human male subjects. Each skin treatment device was initially strained to about 45%+−2% of the initial length l0 of the device. For the particular device used, the initial load on the device was approximately 0.28 N/mm.

Figure 6:
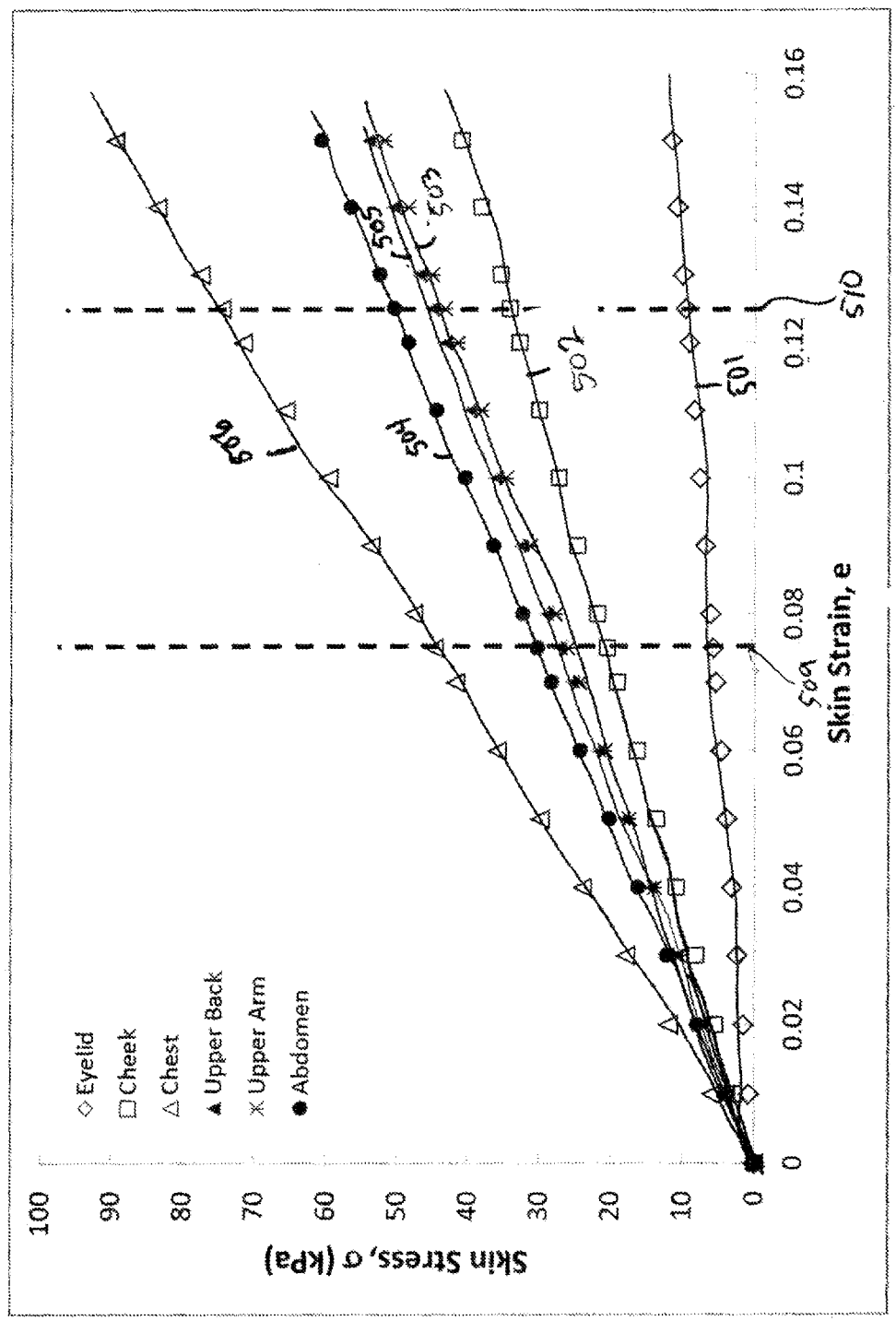

FIGS. 2A1 to 2A6 show the grids prior to application of the skin devices at various skin sites: the eyelid, cheek, upper arm, upper back, abdomen and chest, respectively. FIG. 2B1 to 2B6 show the line deformations at the eyelid, cheek, upper arm, upper back, abdomen and chest, respectively when the skin devices were applied to the noted regions. Arrows indicate direction of device compression.

Digital images were taken of the grids before and after the application of the skin treatment device. Digital image speckle correlation (DISC), a non-contact optical technique, was used to determine strains during loading. Images were taken with the 3D DISC system (Q-400, Dantec Dynamics, Skovlunde, Denmark) and strain maps were generated using Istra 4D software (Dantec Dynamics). Descriptions of such a non-contact technique are described, for example in Marcellier, H., Vescovo, P., Varchon, D., Vacher, P. & Humbert, P. "Optical Analysis of displacement and strain fields on human skin" *Skin Res Technol* 7, 246-253 (2001). And Staloff, I. A. & Rafailovitch," M. Measurement of skin stretch using digital image speckle correlation" *Skin Res Technol* 14, 298-303. The measured strain values were used to determine region-specific differences in skin mechanical properties in humans as described below. A variety of different skin zones showed distinct tensional states. As shown in images in FIG. 2B, digital image speckle correlation (DISC) was utilized to study region-specific responses to device application.

Compressive skin strains, $\epsilon_{skin}$, were calculated based on the DIC analysis, which obtained measured skin strains $\epsilon_{DIC}$, resulting from the forces imparted on the skin surface by the skin treatment device. These measure skin strains, $\epsilon_{DIC}$ were: 28.6±0.4, 22.1±0.4, 21.5±0.4, 19±0.2, 20.6±0.5, and 18.8±0.6% for eyelid, cheek, upper arm, upper back, abdomen and chest, respectively (Table 1). These strains were related to the initial and final dimensions of the device by:

$$\epsilon_{skin} = (l_f - (1+\epsilon_{initial})*l_0)/(1+\epsilon_{Initial})*l_0 \quad \text{(Eq.1)}$$

where $l_0$ is the original length of the device lf is the final dimension (length) of the device on the skin at equilibrium, $100*\epsilon_{Initial}$ is the initial percent strain of the device when loaded, and $(1+\epsilon_{Initial})/l_0$ is the length of the device when initially strained.

The device was initially strained at 45% and thus the measured strains were related to the initial and final dimensions of the device as follows:

$$\epsilon_{DIC} = (l_f - 1.45 l_0)/1.45 l_0 \quad \text{(Eq.2)}$$

The final dimension of the device, lf, was related to the initial dimension of the device and the device strain, $\epsilon_{device}$, at equilibrium by:

$$l_f = l_0 + l_0 \epsilon_{device} \quad \text{(Eq.3)}$$

Using the equations above, the device strain, $\epsilon_{device}$, at equilibrium was defined in terms of the skin strain, $\epsilon_{DIC}$, as:

$$\epsilon_{device} = 0.45 + 1.45 * \epsilon_{DIC} \quad \text{(Eq.4)}$$

The various determined device strains at the various locations are set forth in Table 1.

The device strains ($\epsilon_{device}$) may be used to determine the load (force) per width of the device, ($F_{device}/w$) knowing or approximating the elastic/viscoelastic behavior of the device when strained to a pre-determined amount and then allowed to relax. FIG. 3 illustrates an example of behavior of a particular device during a cycle of loading and unloading. The stress strain curve 300 includes engineering strain versus measured force per width during pre-straining 301 until it is strained to 45% (302) and engineering strain during relaxation 303. These characteristics may vary from device to device, for example, among other things, based on device dimensions, construction, material properties, or material properties over time, the number of times the device is subjected to loading and unloading cycles or other conditions that may affect material properties. A stress strain curve for a device may be obtained using a tensile testing device, a Chatillion (TCD225 system with TLC series load cell, AMETEK, Inc., Largo, Fla., USA). For example, FIGS. 3 and 4 illustrate a stress-strain relationship observed for a device described in Example 1 when loaded by a strain of 45% and then unloaded.

The load per width values at various body locations based on the stress strain curve for the device shown in FIG. 3 and FIG. 4 were determined to be (extrapolated) 5.6±2.4, 42.1±2.2, 45.8±2.7, 50.4±2.5, 58.6±1.2, and 59.7±3.6 N/m for eyelid, cheek, upper arm, abdomen, upper back, and chest, respectively (Table 1).

FIG. 4 illustrates a portion of the stress strain curve 400 for the skin device used in Example 1 during loading 410 and during unloading 420. The load per width of the device when at equilibrium on the eyelid correlates with the measured percent strain of the device on the eyelid at equilibrium 401. The load per width of the device when at equilibrium on the cheek correlates with the measured percent strain of the device on the cheek at equilibrium 402. The load per width of the device when at equilibrium on the upper arm correlates with the measured percent strain of the device on the upper arm at equilibrium 403. The load per width of the device when at equilibrium on the abdomen correlates with the measured percent strain of the device on the abdomen at equilibrium 404. The load per width of the device when at equilibrium on the upper back correlates with the measured percent strain of the device on the upper back at equilibrium 405. The load per width of the device when at equilibrium on the chest correlates with the measured percent strain of the device on the chest at equilibrium 406.

TABLE 1

|  | Skin Strain (%) | Device Strain (%) | Load/Width (Device) (N/m) |
|---|---|---|---|
| Eyelid | 28.6 ± 0.4 | 3.6 ± 0.6 | 5.6 ± 2.4 |
| Cheek | 22.1 ± 0.4 | 13 ± 0.5 | 42.1 ± 2.2 |
| Upper Arm | 21.5 ± 0.4 | 13.8 ± 0.6 | 45.8 ± 2.7 |
| Upper Back | 19.0 ± 0.2 | 17.5 ± 0.3 | 58.6 ± 1.2 |
| Abdomen | 20.6 ± 0.5 | 15.1 ± 0.8 | 50.4 ± 2.5 |
| Chest | 18.8 ± 0.6 | 17.7 ± 0.9 | 59.7 ± 3.6 |

Example 2

In this Example, device strain data and device load (force) per width data from Example 1 were used to determine skin stresses for the eyelid, cheek, upper arm, upper back, abdomen and chest regions as follows:

Using an assumption that the force of the device, Fdevice, adhered to the skin is equal to the force of the skin at equilibrium, the skin stresses, skin, (at the edge or boundary of the device orthogonal to the force direction) can be determined by:

$$\sigma_{skin} = F_{device}/(w \times t) \quad \text{(Eq. 5)}$$

where $F_{device}/w$ is the force per width of the device that correlates with the measured $\epsilon_{device}$ at equilibrium as the device unloads after being loaded by a certain strain and t is the thickness of the skin.

Skin thicknesses for the eyelid, cheek, upper arm, upper back, abdomen and chest regions were measured using a 10-5 MHz linear array ultrasound transducer (SonoSite M-Turbo, United Medical Instruments, Inc. San Jose, Calif.), as described in Gurtner, G. C., et al. "Improving cutaneous scar by controlling the mechanical environment: large animal and phase I studies", *Ann Sur* 2011; 00:1-9, incorporated in its entirety herein by reference. The measured skin thickness values were: 0.53±0.15, 1.43±0.07, 1.31±0.10, 1.46±0.29, 1.16±0.15, and 1.0±0.14 mm for eyelid, cheek, upper arm, upper back, abdomen, and chest, respectively. According to variations skin thicknesses at other skin regions may be similarly estimated.

In addition to the measured values, published skin thickness values were used to provide an estimated range of thickness values for each region. The skin data used was published in Barker D E (1951) Skin thickness in the human. *Plast Reconstr Surg* 7: 115-116; Artz C P, Moncrief J A, Pruitt B A Jr (1979) Burns: a team approach. Saunders, Philadelphia, pp. 24-44; and Lee Y, Hwang K (2002) Skin thickness of Korean adults. *Surg Radiol Anat* 24: 183-189.

Using the average of both measured and published thickness values for a particular region of skin, the stress values were determined. For purposes of a variation herein, it is assumed that the thickness in a region is similar or generally the same from subject to subject within a range. It is further noted that equilibrium of moment forces were not considered in the estimates in this example. Skin stresses determined accordingly are set forth in Table 2 with standard deviations from measured and published thickness values for a particular region of skin. Standard deviations in stress values were calculated taking both the error in force per width and thickness values into consideration. According to variations, skin thicknesses may be measured, estimated using known or published data, or may use both measured and estimated data as described above.

TABLE 2

|  | Strain (% compression) | Device Strain (%) | Load/Width (N/m) | Skin Thickness (mm) | Stress (kPa) |
| --- | --- | --- | --- | --- | --- |
| Eye | 28.6 ± 0.4 | 3.6 ± 0.6 | 5.6 ± 2.4 | 0.51 ± 0.13 | 11.0 ± 5.5 |
| Cheek | 22.1 ± 0.4 | 13 ± 0.5 | 42.1 ± 2.2 | 1.39 ± 0.20 | 30.2 ± 4.7 |
| Upper Back | 19.0 ± 0.2 | 17.5 ± 0.3 | 58.6 ± 1.2 | 1.71 ± 0.30 | 34.3 ± 6.0 |
| Upper Arm | 21.5 ± 0.4 | 13.8 ± 0.6 | 45.8 ± 2.7 | 1.23 ± 0.15 | 37.2 ± 5.0 |
| Abdomen | 20.6 ± 0.5 | 15.1 ± 0.8 | 50.4 ± 2.5 | 1.21 ± 0.21 | 41.7 ± 7.7 |
| Chest | 18.8 ± 0.6 | 17.7 ± 0.9 | 59.7 ± 3.6 | 1.06 ± 0.24 | 56.1 ± 12.9 |

Example 3

In this example desired initial strain values (the amount of strain in the device prior to its application on skin) of the device in Example 1 were estimated or approximated. A desired range of resulting skin strain values between 15% and 25% resulted in estimated desired initial strains for various regions using the device described in Example 1. The desired initial strain for the eyelid ranged from 21% to 38%. The desired initial strain for the cheek was about between 23% and 45%. The desired initial strain for the abdomen was about between 31% and 57%. The desired initial strain for the chest was about between 34% and 64%.

Figure 5:
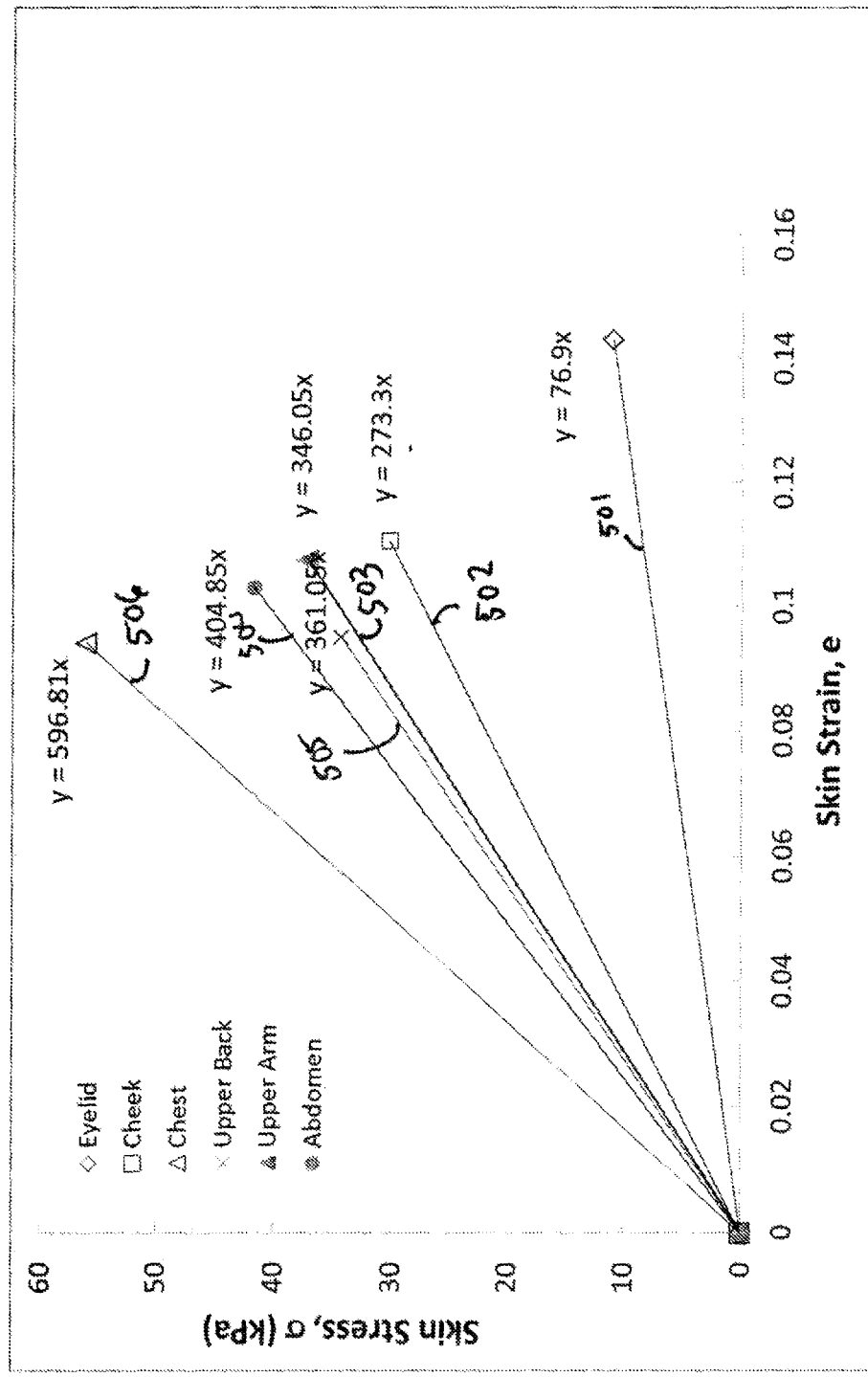
FIG. 5 is a graphical representation of determined skin stress vs. skin strain corresponding to Examples 1, 2, and 3.

The desired initial strain values were determined by plotting the stress vs. strain at the edges of the dressing for each skin location as shown in FIG. 5. An assumption was made that for purposes of estimating the initial strain value, the stress vs. strain behavior of skin is linear at lower values of stress and strain. This is a valid assumption for typical strain values experienced with physiological loading conditions (<20%). It was further assumed that the tensile strain at the edges of the device parallel to the strain direction was ½ of the compressive strain imparted to the skin by the device. The approximated linear curves for each skin zone are shown respectively as eyelid 501, cheek 502, upper arm 503, abdomen 504, upper back 505 and chest 506.

As shown in FIG. 6, using the stress strain curve, the skin stress, $\sigma_{skin}$, values that would be experienced at the edges of the device when skin strains of 15% to 25% (shown as lines 509, 510 respectively) were imposed on eyelid, cheek, upper arm, abdomen, upper back and chest skin were extrapolated using the estimated linear curves for each skin area (respectively eyelid 501, cheek 502, upper arm 503, abdomen 504, upper back 505 and chest 506) skin or zone as shown in FIG. 5. Then, the force per width of the skin, $F_{skin}/w$, at the edges of the device for each location was calculated using:

$$F_{skin}/w = \sigma_{skin}/t \qquad (Eq.6)$$

where t is the thickness of skin. Then, using the assumption that the force of the device, $F_{device}$, adhered to the skin is equal to the force of the skin at equilibrium, the force per width of the device, $F_{device}/w$, at equilibrium was calculated using:

$$F_{device}/w = F_{skin}/w \qquad (Eq.7)$$

Then, the device strain data and device load (force) per width data from Example 1 were used to determine the $\epsilon_{device}$ at equilibrium (after the device unloads after being loaded by a certain strain) that correlates with the force per width of the device for each body location. Finally, the desired initial device strain, $\epsilon_{Initial}$, which would impart the $\epsilon_{device}$ at equilibrium, was determined for a range of resulting skin strain values, $\epsilon_{skin}$, between 15% and 25% for each body location by plugging Eq.3 to Eq.1 and solving for $\epsilon_{Initial}$:

$$\epsilon_{Initial} = (\epsilon_{device} - \epsilon_{skin}/(1+\epsilon_{skin}) \qquad (Eq.8)$$

Table 3 illustrates exemplary calculations of a desired initial device strain for the device described in Example 1.

Example 4

Figure 8:
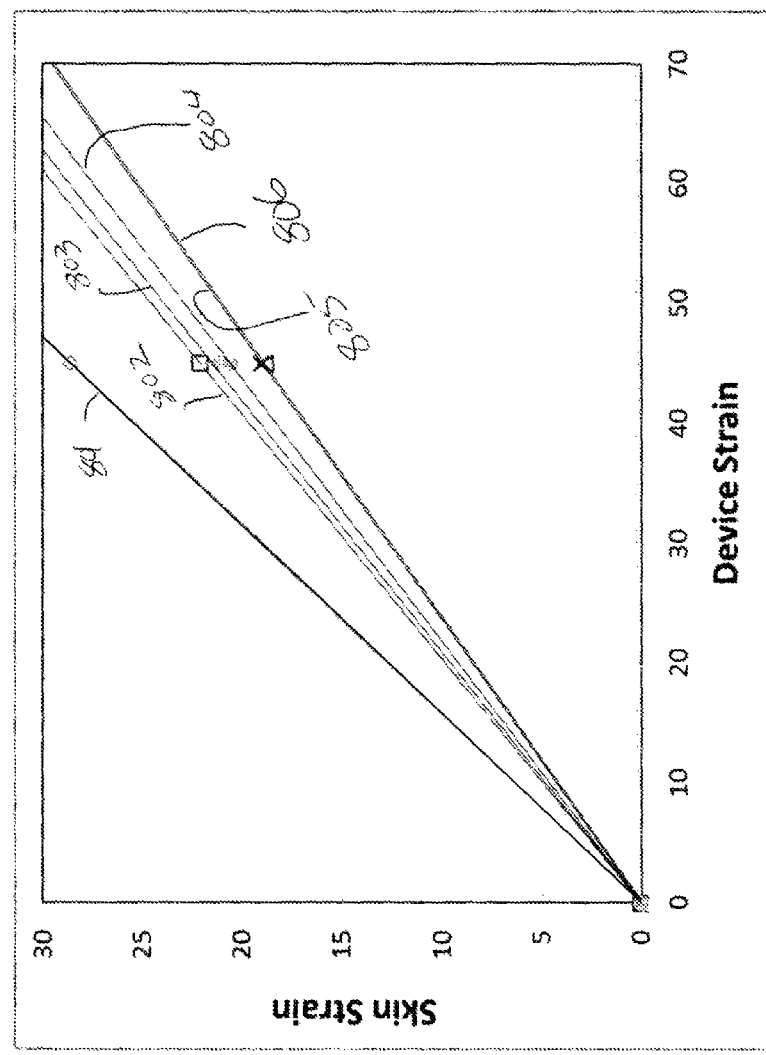
FIG. 8 is a graphical representation of approximate initial device strain versus skin strain for various body regions corresponding to Example 4.

Additionally or alternatively to estimating desired initial strain values, as described in Example 3, initial strain values (the amount of strain in the device prior to its application on skin) of the device in Example 1 may be estimated or approximated, for example using the curves shown in FIG. 8.

As shown in FIG. 8 curves 801, 802, 803, 804, 805, 806 for initial device strain versus skin strain were generated respectively for eyelid, cheek, upper arm, abdomen, upper back and chest by plotting the measured skin strain values at an initial device strain of 45% as set forth in Tables 1 and 3. An assumption is made that an approximately or generally linear relationship exists between resulting skin strain and initial device strain. As further shown in Table 3 initial device strain values for the various body regions or locations may be extrapolated from the curves 801-805 at desired final strain values, e.g. between 15% and 25% skin strain.

TABLE 3

| Body Region or Location | Skin Strain (inside) (% compression) | Skin Strain (outside) (% tension) | Skin Stress (outside) (kPa) | Skin Thickness (average) (mm) | Load/Width (average) (N/m) | Final Device Strain (%) | Initial Device Strain Ex. 3 (%) | Initial Device Strain Ex. 4 (%) |
|---|---|---|---|---|---|---|---|---|
| Eyelid | 15 | 7.5 | 5.8 | 0.51 | 2.9 | 3 | 21.2 | 24 |
|  | 25 | 12.5 | 9.6 | 0.51 | 4.9 | 3.5 | 38.0 | 39.5 |
| Cheek | 15 | 7.5 | 20.5 | 1.39 | 28.5 | 9.4 | 28.6 | 30 |
|  | 25 | 12.5 | 34.2 | 1.39 | 47.5 | 14.2 | 52.3 | 51 |
| Upper Back | 15 | 7.5 | 27.1 | 1.71 | 46.3 | 14.0 | 34.1 | 36 |
|  | 25 | 12.5 | 45.1 | 1.71 | 77.2 | 22.6 | 63.4 | 60 |
| Upper Arm | 15 | 7.5 | 26.0 | 1.23 | 26.0 | 10.3 | 29.7 | 31.5 |
|  | 25 | 12.5 | 43.3 | 1.23 | 43.3 | 16.0 | 54.6 | 52.5 |
| Abdomen | 15 | 7.5 | 30.4 | 1.21 | 36.7 | 11.4 | 31.1 | 33 |
|  | 25 | 12.5 | 50.6 | 1.21 | 61.2 | 18.0 | 57.3 | 55 |
| Chest | 15 | 7.5 | 44.8 | 1.06 | 47.4 | 14.2 | 34.4 | 66 |
|  | 25 | 12.5 | 74.6 | 1.06 | 79.1 | 23.1 | 64.1 | 60 |

In accordance with variations of the invention, a skin treatment device may be selected with desired mechanical or force properties based on the location where the skin treatment device is to be applied and/or other demographic or individual patient information.

According to variations, the characteristics of the location where the skin treatment device is to be applied may be determined, estimated or approximated using one of a variety of methods. For example such methods or techniques may include but are not limited to: measuring, determining, estimating or approximating a relative amount of skin tension or stiffness using a device (for example, device 100 described with respect to FIG. 1A to 1F or other pressure suction devices, or acoustics); measuring, determining, estimating or approximating relative inherent skin stress by observing skin characteristics such as stresses, skin strain after application of a skin treatment device; using measured or published data; and/or further characterizing the skin based on patient demographic information. According to some variations measurements of pre-surgical areas may be correlated with post-surgical properties of the skin of the area.

According to variations properties of a device or devices may exhibit one or more desired force properties (that may be location, patient or demographic dependent) such as, load per width of the device at equilibrium, initial strain of the device, or strain or stress imparted to the skin of a particular location by the device.

The desired force property or properties may be determined, estimated or approximated in a variety of manners.

According to variations of the invention, force properties of a device may be selected based on relative stresses, stiffness or tension, of the region of skin. For example for the stiffer regions or regions with higher stresses or tension, a skin device with greater initial device strain, greater load per width or other properties may be selected. For example for the less stiff, lower stress, lower tension regions, a skin device with less initial strain, less load per width force or other properties may be selected. For example, a skin device may be selected to unload at least a portion of the skin tension or stresses at a particular region, location or area. A skin stiffness, stress or tension characteristic of a skin region may also be based on its actual or approximated or relative stiffness, stress or tension with respect to other locations within a range of skin strains. A relative stiffness, stress, or tension may be based on a comparison from skin region to skin region, from subject to subject, and/or based on a comparison of a standard with respect to a subject.

According to variations, a device may be selected from one or more devices with different force properties or levels of force properties. One or more of the plurality of device property categories may be selected to better fit a particular skin region and/or a particular subject based, for example on actual, approximated or relative skin stiffness, stress or tension characteristics.

For example, a relatively stiffer (determined by force/width) region may use a device that is strained in an amount that provides a force/width of about 45 to 80 N/m. A region with a relatively upper mid-range stiffness region may use a device that is strained in an amount that a force/width of about to 35 to 65 N/m. A region with a relatively upper mid-range stiffness region may use a device that is strained in an amount that a force/width of about to 25 to 45 N/m. A relatively less stiff region may use a device that is strained in an amount that provides a force/width of about 1 to 25 N/m. These load per width values may vary substantially based on region of skin, particular factors related to an individual subject, or type of treatment provided by the skin treatment device.

These regions or other mechanically differentiated skin regions described herein may be generally identified using a device such as device 100 where a stiffer region might be indicated by B, relatively less stiff region by C and an even lesser stiff region by D.

As an additional example, for a chest or upper back region a device may exhibit a relatively greater stiffness. For example, a cheek or abdomen region may exhibit a relatively mid-range stiffness. For example, for an eyelid region may exhibit a relatively less stiff region Different devices may be selected for these different regions.

According to some variations, at a given region, a device may be used that provides a desired or sufficient stress off-loading for a particular application. As an additional example a device with relatively greater stress offloading mechanical properties may be selected or used for a region with relatively greater skin tension or stiffness; a device with relatively mid-range stress off-loading mechanical properties may be selected or used for a region with relatively mid-range skin tension or stiffness; and/or a device with relatively less stress off-loading mechanical properties may be selected or used for a region with relatively less skin tension or stiffness.

As an example a device with relatively greater stress offloading mechanical properties may be selected or used for the chest or upper back region; a device with relatively mid-range stress off-loading mechanical properties may be selected or used for the abdomen cheek region; and/or a device with relatively less stress off-loading mechanical properties may be selected or used for the eyelid region.

According to variations for a desired skin strain or range of skin strain amounts, an initial strain of a device may be selected. For example a resulting skin strain of between about 10% and 30%, between 15% and 25% or between 18% and 23% or for any strain or given range of strains may be desired. The initial strain value may be determined, approximated or estimated for example as described with respect to Example 3 herein.

According to variations an initial device strain may be selected from within one or more ranges. For example the one or more ranges may be from about 20% to 40%; from about 25% to about 55%; and/or from about 30 to about 65%; or number ranges within these ranges. An applicator or tensioning device may have one or more strain values selectable based on the region or other characteristic of a skin region to which it is to be applied.

For example for a range of resulting skin strain of between 15% and 25% using a device similar to that described in Example 1, for an eyelid, an initial device strain may be between approximately 21% to 40%; for a cheek approximately 28% to 53%; for an upper back 34% to 64%; for an upper arm 29% to 55%; for an abdomen 31% to 58%; for a chest region about 34% to 65%. These numbers may be adjusted based on slippage resulting from adhesive slippage of the adhesive used to apply the dressing to the skin. The slippage for a particular adhesive may be determined a number of ways including by empirical observation.

According to a variation, curve generally representing the force versus strain of a particular skin device (see e.g. FIG. 3) during loading and unloading may be used to identify or select a desired device with desired device properties. A characteristic curve of a skin device may be used to approximate or determine the load per width of the skin treatment device, device strain, skin strain, and/or stress value, when the device is strained to a given level, applied to skin and allowed to reach a force equilibrium. For example, knowing device strain levels at equilibrium at a particular location of a subject's skin, load per width of the device at equilibrium can be estimated using the characteristic curve for the device at a particular initial pre-strain. It is noted that the characteristic curve may vary from device to device; may vary after repeated cycles of loading and unloading and may vary depending on the amount the device is strained during loading. In some variations, it may be assumed that the curve is similar for some levels of strain.

According to variations, a user may select a skin treatment device from a plurality of skin treatment devices, each having different force properties when strained a given or set amount. A tensioning device, stretching device or applicator that pre-strains a device a preset amount may then be used to pre-strain any one of the selected devices. For example when applied to a particular location, a first device when strained the pre-set amount may provide a lower load per width at equilibrium or may provide less skin strain at equilibrium while a second device when strained the pre-set amount may provide a greater load per width at equilibrium or a greater skin strain at equilibrium than the first device.

The ranges of desired force properties described herein may be adjusted for individual patients. Such adjustments may be based on factors such as relative stiffness, stress or tension measurements, for example, using the device 100 described herein; based on one or more individual factors, based on a subject's irritation or other response to skin stresses, based on desired outcome or use of the skin treatment device which may include but is not limited scar amelioration or prevention.

While these various methods shown may be used to approximate device properties, other methods are contemplated herein. For example, the modulus of elasticity of skin may be determined by obtained observing the skin strain using a device at a plurality of initial strain levels. Values determined may be confirmed or further approximated with a variety of measurements or experimentation.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

The invention claimed is:

1. A method of treating a subject to ameliorate scar formation, comprising:
    measuring a skin tension property of a skin location of a subject;
    providing a skin treatment device wherein the skin treatment device comprises:
    an elastic member configured to be stretched; and
    a securing member configured to couple the skin treatment device to the subject;
    then selecting an initial strain amount from a plurality of predetermined strain amounts to be applied to a skin treatment device based on the measured skin tension property of the skin location and applying the initial strain amount to the skin treatment device to form an initial strained configuration;
    securing the skin treatment device to the skin of a subject at or near the skin location; and
    releasing the skin treatment device from the initial strained configuration while attached to the subject, to thereby offload skin tension at or near the skin location.

2. The method of claim 1, wherein the skin tension property comprises an inherent skin tension.

3. The method of claim 1, wherein the skin tension property comprises a relative skin tension.

4. The method of claim 1, wherein the skin tension property comprises skin stiffness.

5. The method of claim 1, wherein the skin tension property comprises a skin deformation property.

6. A system for treating a subject, comprising:
    a skin treatment device comprising an elastic member and a securing member configured to couple the device to a skin of the subject, wherein the elastic member has unstrained configuration and a plurality of selectable strained configurations; and
    a skin tension device configured to measure a relative skin tension, wherein the skin tension device comprises an indicator, the indicator configured to indicate at least one of the plurality selectable strained configurations based upon the relative skin tension measured by the skin tension device; and
    wherein the plurality of selectable strained configurations of the skin treatment device is indicated on the skin treatment device.

7. The system of claim 6, wherein the skin tension device comprises a mechanical skin tensioning structure configured to apply a tension to skin at a skin location, wherein the plurality of indicators correspond to skin response to tension applied by the mechanical skin tensioning structure.

8. The system of claim 6, wherein each of the plurality of selectable strained configurations comprises a percentage of strain.

9. The system of claim 6, wherein each of the plurality of selectable strained configurations correspond to a force property to be applied by the skin treatment device to skin.

10. The system of claim 9, wherein the force property is a load per width to be applied by the skin treatment device to skin when at force equilibrium with the skin.

11. The system of claim 9, wherein the force property corresponds to a desired offloading of skin tension at a skin location.

12. The method of claim 6, wherein measuring the skin tension property comprises:
applying an energy to the skin location of the subject using a skin interface element; and
measuring the skin tension property based upon a response of the skin location to the skin interface element.

13. A system for treating a subject comprising:
a skin treatment device comprising an elastic member and a securing member configured to couple the device to a skin of a subject, wherein the elastic member has an unstrained configuration and a plurality of selectable strained configurations each having a predetermined strain amount;
a tensioning member configured to strain the skin treatment device to each of the plurality of selectable strained configurations; and
a strain selector configured to indicate a selected one of the plurality of selectable strained configurations of the elastic member; and
wherein the strain selector comprises a skin tension measuring device configured to determine a relative skin tension at a skin location, wherein the skin tension measuring device comprises a plurality of indicators each configured to indicate a different one of the plurality selectable strain values.

14. The system of claim 13, wherein the skin tension measuring device comprises a mechanical skin tensioning structure configured to apply a tension to skin at a skin location, wherein the plurality of indicators correspond to skin response to tension applied by the mechanical skin tensioning structure.

15. The system of claim 13, wherein each of the plurality of selectable strained values correspond to a force property to be applied by the skin treatment device to skin.

16. The system of claim 15, wherein the force property is a load per width to be applied by the skin treatment device to skin when at force equilibrium with the skin.

17. The system of claim 15, wherein the force property corresponds to a desired resulting skin strain.

18. The system of claim 15, wherein the force property corresponds to a desired offloading of skin tension at the skin location.

19. The method of claim 1, wherein measuring the skin tension property comprises:
applying an energy to the skin location of the subject using a skin interface element; and
measuring the skin tension property based upon a response of the skin location to the skin interface element.

20. The method of claim 19, further comprising providing a visual indicator of the skin tension property.

21. The method of claim 20, wherein measuring the skin tension property is performed using a tool, and the visual indicator is located on the tool.

22. The method of claim 20, wherein selecting a skin treatment device comprises matching the visual indicator of the skin tension property to a corresponding visual indicator on a skin treatment device from a plurality of skin treatment devices.

23. The method of claim 19, wherein the energy is selected from a group consisting of mechanical energy.

24. The method of claim 19, wherein the energy is selected from a group consisting of vibrational energy.

25. The method of claim 19, wherein the energy is selected from a group consisting of acoustical energy.

* * * * *